(12) United States Patent
Vogt et al.

(10) Patent No.: US 12,285,198 B2
(45) Date of Patent: Apr. 29, 2025

(54) DEVICE FOR THE LOCAL APPLICATION OF AND/OR FOR FLUSHING WITH PHARMACEUTICAL FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 1149 days.

(21) Appl. No.: 17/029,477

(22) Filed: Sep. 23, 2020

(65) Prior Publication Data
US 2021/0113251 A1 Apr. 22, 2021

(30) Foreign Application Priority Data
Oct. 17, 2019 (EP) .................................... 19203785

(51) Int. Cl.
*A61B 17/86* (2006.01)
*A61B 17/80* (2006.01)
(Continued)

(52) U.S. Cl.
CPC ...... *A61B 17/8625* (2013.01); *A61B 17/8042* (2013.01); *A61B 17/864* (2013.01);
(Continued)

(58) Field of Classification Search
CPC ............ A61B 17/8625; A61B 17/8042; A61B 17/864; A61B 17/8685; A61B 2017/561;
(Continued)

(56) References Cited

U.S. PATENT DOCUMENTS

| 2,073,372 A | * | 3/1937 | Heidbrink ............. | A61M 16/10 73/861.57 |
| 4,653,489 A | | 3/1987 | Tronzo | |

(Continued)

FOREIGN PATENT DOCUMENTS

| DE | 3508759 | 10/1985 |
| DE | 29914192 U1 | 10/1999 |

(Continued)

OTHER PUBLICATIONS

PJ Technologies Medical Devices. "Practical Guide—BeeLine Infusion". <https://beelineinfusion.com/pdf-guide/> (Year: 2023).*

*Primary Examiner* — Nathan R Price
*Assistant Examiner* — Haden Matthew Ritchie
(74) *Attorney, Agent, or Firm* — Dicke, Billig & Czaja, PLLC

(57) ABSTRACT

A device having a bone screw with a body, an outer thread and a proximal screw head. A fluid-permeable conduit is disposed in the body, begins at the head and opens out into a fluid outlet opening that is spaced apart from the head in the distal direction. An axial groove extends from the fluid outlet opening to the screw head. The base of the groove is deeper than the base of the outer thread. A cap detachably connects with the screw head, in which a fluid-permeable conduit is disposed, which opens out into the conduit of the bone screw. A hose for feeding fluid is connected or connectable in a fluid-permeable manner with the inlet opening on the cap so that a pharmaceutical fluid is pressable out of the fluid outlet opening through the hose, through the conduit of the cap and through the conduit of the bone screw.

20 Claims, 12 Drawing Sheets

(51) Int. Cl.
*A61M 5/14* (2006.01)
*A61M 5/145* (2006.01)
*A61M 5/168* (2006.01)
*A61M 39/10* (2006.01)
*A61B 17/56* (2006.01)
*A61M 39/00* (2006.01)
*A61M 39/02* (2006.01)

(52) U.S. Cl.
CPC ....... *A61B 17/8685* (2013.01); *A61M 5/1454* (2013.01); *A61M 5/16881* (2013.01); *A61B 2017/561* (2013.01); *A61M 2039/0009* (2013.01); *A61M 2039/025* (2013.01); *A61M 2039/0276* (2013.01); *A61M 2039/0288* (2013.01); *A61M 39/1011* (2013.01)

(58) Field of Classification Search
CPC ............ A61M 5/1454; A61M 5/16881; A61M 39/1011; A61M 2039/0009; A61M 2039/025; A61M 2039/0276; A61M 2039/0288
See application file for complete search history.

(56) References Cited

U.S. PATENT DOCUMENTS

| | | | | |
|---|---|---|---|---|
| 5,332,398 | A * | 7/1994 | Miller | A61M 39/0208 604/175 |
| 5,601,559 | A | 2/1997 | Melker et al. | |
| 6,048,343 | A | 4/2000 | Mathis et al. | |
| 6,214,012 | B1 * | 4/2001 | Karpman | A61B 17/864 606/92 |
| 8,382,808 | B2 | 2/2013 | Wilberg et al. | |
| 8,974,505 | B2 | 3/2015 | Sawa et al. | |
| 9,326,801 | B2 | 5/2016 | Poulos | |
| 9,616,205 | B2 | 4/2017 | Nebosky et al. | |
| 10,188,442 | B2 | 1/2019 | Mazel | |
| 10,349,993 | B2 | 7/2019 | Nebosky et al. | |
| 10,357,298 | B2 | 7/2019 | Nebosky et al. | |
| 2001/0007074 | A1 * | 7/2001 | Strobel | A61B 17/8615 606/305 |
| 2001/0021852 | A1 | 9/2001 | Chappius | |
| 2005/0015059 | A1 | 1/2005 | Sweeney | |
| 2005/0059972 | A1 | 3/2005 | Biscup | |
| 2006/0229573 | A1 * | 10/2006 | Lamborne | A61M 25/007 604/263 |
| 2006/0241623 | A1 * | 10/2006 | Lim | A61B 17/8625 606/265 |
| 2010/0030135 | A1 | 2/2010 | Mitchell | |
| 2011/0060373 | A1 * | 3/2011 | Russell | A61B 17/0401 606/86 R |
| 2011/0282418 | A1 * | 11/2011 | Saunders | A61F 7/12 606/301 |
| 2012/0029578 | A1 | 2/2012 | Suh | |
| 2012/0095440 | A1 * | 4/2012 | Islam | A61M 39/0208 604/506 |
| 2013/0172939 | A1 * | 7/2013 | Ziolo | A61B 17/8605 606/301 |

FOREIGN PATENT DOCUMENTS

| | | |
|---|---|---|
| EP | 0305417 B1 | 6/1995 |
| EP | 0595782 B1 | 6/1998 |
| EP | 1622529 B1 | 12/2011 |
| EP | 2887899 B1 | 8/2017 |
| RU | 2572481 C1 | 1/2016 |
| RU | 2622613 C2 | 6/2017 |
| WO | 2018/175437 A1 | 9/2018 |

* cited by examiner

DEVICE FOR THE LOCAL APPLICATION OF AND/OR FOR FLUSHING WITH PHARMACEUTICAL FLUIDS

RELATED APPLICATION

This application claims the benefit of priority to European Patent Application No. 19203785.1 filed on Oct. 17, 2019, the contents of which are incorporated in this application by reference.

TECHNICAL FIELD

The invention relates to a device for the temporary local application of pharmaceutical fluids and/or for flushing with pharmaceutical fluids.

BACKGROUND OF THE DISCLOSURE

The local application of pharmaceutical active ingredients such as antibiotics has already been known for decades and is particularly beneficial for the treatment or abatement of bone tissue infections. Here, a differentiation can be made between non-reabsorbable and reabsorbable or biodegradable active ingredient carriers.

Screw and plate osteosyntheses have proven their suitability in the surgical treatment of bone fractures for years. Screw and plate osteosyntheses are used with both closed fractures and open fractures for the repositioning and stabilization of the bone fractures. With open fractures, the exposed bone tissue can naturally be contaminated with microorganisms. These infections constitute serious illnesses. In rare cases, however, the bone tissue may also become infected following an operation on a closed fracture. These infected fractures are difficult and complicated to treat. There are a plurality of different treatment options. One frequently used procedure consists of first removing the complete osteosynthesis material and then debriding the infected tissue. Then, local antibiotic carriers are frequently used as implants, which, following implantation, release Gentamicin or other antibiotics over a relatively short space of time, such as collagen sponges and polymethyl methacrylate chains containing Gentamicin. In cases of infection with Gentamicin-resistant and also multiresistant microorganisms, these Gentamicin-releasing active ingredient carriers are not sufficiently effective. A further problem is that the fractured bone also has to be mechanically stabilized. This is particularly difficult when the screw bore holes are also affected by the infection. In such cases, an external fixator is often used, wherein new screws are used outside the infection bone area to affix the external fixator into the bone tissue. This requires additional bore holes in the bone. Alternatively, suction-flush drainage procedures can also be used with larger infected bone areas. With small and medium-sized infected bone tissue, conventional suction-flush drainage procedures can in some cases be difficult to carry out. Bone screws would be desirable that could release pharmaceutical active ingredients directly in or on infected bone tissue and which at the same time could stabilize the fractured bone in a similar way to convention bone screws.

Bone screws with a central conduit in the screw body and windows connected thereto are known as cannulated and fenestrated screws. To date, these bone screws are substantially used in the spinal region as so-called cannulated and fenestrated pedicle screws. Here, bone cement paste is injected through the conduit of the screws into the usually osteoporotic vertebral body. In most cases, a cement coat develops that is coaxial to the longitudinal axis of the pedicle screw. The bone cement then hardens and forms an abutment for the pedicle screws. A plurality of cannulated and fenestrated bone screws have been proposed. Examples of these include the patent specifications and unexamined applications DE 35 08 759 A1, RU 2 572 481 C1, RU 2 622 613 C2, US 2001/0021852 A1, US 2005/0015059 A1, US 2012/0029578 A1, U.S. Pat. No. 6,214,012 B1, U.S. Pat. No. 9,326,801 B2, U.S. Pat. No. 8,382,808 B2 and U.S. Pat. No. 8,974,505 B2.

EP 1 622 529 B1 presents a specially cannulated and fenestrated bone screw. Here, a guide element is temporarily inserted into the conduit of the bone screw. The guide element is used to inject bone cement paste.

A similar adapter for screwing in a cannulated and fenestrated bone screw is disclosed in U.S. Pat. No. 6,048,343 A. The adapter has a longitudinal conduit and seals off the proximal bore hole of the bone screw with its outer wall so that fluids can be pressed into the bone screw through the adapter. The adapter is removed after the fluid has been pressed into the bone.

A screw described in U.S. Pat. No. 10,188,442 B2 is designed for tumor treatment and has three or multiple longitudinal conduits in the screw body which are fenestrated. These longitudinal conduits are provided for connecting to catheters. With the connected catheters, fluid active ingredients can be applied in the bones surrounding the screw.

A bone screw fitted with continuous longitudinal slits, in which the screw head also has a longitudinal slit, is proposed in EP 2 887 899 B1. The longitudinal slits of the screw body are intended to enable improved release of substances such as bone cement from the bone screw.

The patent EP 0 305 417 B1 describes a bone screw that is cannulated and fenestrated. This bone screw is screwed in the bone in a vacuum-tight manner. A suction-flush system is described alongside this bone screw. Here, a flushing fluid is introduced with one cannulated and fenestrated bone screw, and, on a second cannulated and fenestrated bone screw, the flushing fluid is suctioned with a vacuum.

In U.S. Pat. No. 5,601,559 A1, a cannulated and fenestrated bone screw is described that is designed to enable a systematic application of pharmaceutical active ingredients via the bone tissue instead of venous access.

A self-cutting bone screw with longitudinal slits and a central conduit is disclosed in EP 0 595 782 B1. The slit and the conduit are designed to first hold the bone material that is cut when the screw cuts in, and then to enable the bone tissue to grow through the bone screw. In this case, a slit in which multiple openings to the inner conduit are disposed extends into the thread, but not through to the screw head. The conduit and the slit are blocked when the bone screw cuts in through bone material and can then no longer be used to direct a pharmaceutical fluid.

U.S. Pat. No. 10,357,298 B2, U.S. Pat. No. 10,349,993 B2 and U.S. Pat. No. 9,616,205 B2 disclose implants and an implantable screw therewith that contains a longitudinal conduit with fenestrations. In the longitudinal conduit, a taper is disposed below a screw head that increases in the distal direction. Below this taper, there is a reservoir with conduits that lead outwards. The diameter of the conduit in the screw head is the same as the diameter of the reservoir. The length of the conduits starting from the reservoir is greater than the inner diameter of said conduits.

An object of the invention is to overcome the disadvantages of the prior art. In particular, a device shall be provided for the local application of and flushing with pharmaceutical fluids such as antibiotic solutions, said device enabling a local and temporary delivery of the pharmaceutical fluid in the region of the bone, for example in infected bones that are affixed with bone screws and osteosynthesis plates. The device should also be suitable for the repeated delivery of the pharmaceutical fluid over long periods of time and at a specific site without the device having to be removed for this purpose. It shall be possible to manufacture the device at low cost. The treatment with the device should be adaptable with regard to the procedure, so that it is possible to react to a change in the treatment situation or to an absence of success.

An object of the invention is thus also to develop a device in the form of a local application and flushing system for pharmaceutical fluids that is designed for the prevention as well as the treatment of periprosthetic infections of screw and plate osteosyntheses and for the simultaneous repositioning and mechanical stabilization of fractured bones. The application and flushing system to be developed should enable local application and preferably also flushing with pharmaceutical fluids with at least partial soft tissue coverage over a period of several days to weeks. No antimicrobial active ingredient carriers should themselves be contained in the device parts, particularly in the bone screws of the device. In contrast, any antiseptic or antibiotic solutions should be applicable in the region of the bone of a patient to be treated. Furthermore, to exclude the possibility of embolisms, it is important that during the application of pharmaceutical fluids, no overpressure can develop in the marrow area. In the case of plate osteosyntheses, it is desirable that the pharmaceutical fluids can also reach the parts of the osteosynthesis plates that abut the bone screws. The bone screws in the device should essentially correspond to the dimensions and the design of standard bone screws. The bone screws in the device should enable a mechanical fixation of the fracture ends in the case of the screw osteosynthesis, and a normal mechanical fixation of the osteosynthesis plates on the bone tissue in the case of plate osteosynthesis. The device or the application and flushing system should be designed such that following completion of the introduction of pharmaceutical fluids, the modified bone screws can remain in the bone tissue in the same way as the standard bone screws, if this is medically required. It is further envisaged that a return flow of the pharmaceutical fluids outside the human body is possible. It is important that pharmaceutical fluids of any composition and preferably also of a modifiable composition can be used.

SUMMARY OF THE DISCLOSURE

The objects of the invention are achieved by a device for the local application of and/or flushing with pharmaceutical fluids, said device having:
  at least one bone screw, the at least one bone screw having a screw body, an outer thread and a proximal screw head, wherein at least one conduit is disposed in the screw body, wherein the at least one conduit is fluid-permeable, begins at the screw head and opens out into at least one fluid outlet opening in the screw body, wherein the at least one fluid outlet opening is spaced apart from the screw head in the distal direction,
  at least one axial groove penetrating the outer thread of the bone screw which extends from the at least one fluid outlet opening in the screw body through to the screw head, wherein a base of the groove of the at least one axial groove is deeper in the screw body than a base of the outer thread,
  at least one cap with a connecting element for the detachable connection of the at least one cap with the proximal screw head of the at least one bone screw, wherein a fluid-permeable conduit is arranged in the at least one cap, wherein said conduit in the at least one cap opens out into the at least one conduit of the at least one bone screw when the at least one cap is detachably connected via the connecting element to the at least one bone screw, and wherein the conduit begins at an inlet opening in the at least one cap, and
  at least one hose for feeding fluid which is connected or connectable in a fluid-permeable manner with the inlet opening on one of the at least one cap, so that a pharmaceutical fluid is pressable from the at least one fluid outlet opening with a pressure through the at least one hose for feeding fluid, through the conduit of the at least one cap and through the at least one conduit of the at least one bone screw when the at least one hose for feeding fluid is connected to the at least one cap and the at least one cap is connected via the connecting element with the at least one bone screw.

The axial direction of the bone screw extends from the screw head to an opposite (distal) screw end (the tip) of the bone screw. The term "axial" refers in this case to this screw axis. Here, the screw axis is also the axis around which the at least one bone screw is rotated when it is being screwed in or out. The thread of the bone screw therefore runs around this screw axis.

The fact that the groove base of the groove is deeper than the base of the outer thread means that the groove is cut in deeper into the screw body than the outer thread. The groove base is the deepest point of a groove, in the same way that a thread base is understood to be the deepest point of a thread.

According to the invention, the at least one fluid outlet opening is therefore spaced apart from the screw head. Preferably, the at least one fluid outlet opening is disposed in the region of a distal screw end. The fact that the at least one conduit opens out into at least one fluid outlet opening in the region of a distal screw end means that the at least one fluid outlet opening is disposed closer on the distal screw end of the bone screw than the screw head. Preferably, the at least one fluid outlet opening is disposed closer to the distal screw end of the bone screw than on the screw head. Particularly preferably, the at least one fluid outlet opening is disposed within 5 mm of a distal end of the outer thread of the bone screw.

The term "bone screws" should in this case be understood to refer to all screws commonly used in bone surgery. The device according to the invention or the application and flushing system according to the invention is particularly preferably usable as the at least one bone screw with cortical screws and/or cancellous screws. The at least one bone screw is therefore preferably at least one cortical screw and/or cancellous screw.

The bone screws can have any desired inner and outer drives. Frequently, Torx and Allen drives are used in surgery, which are also preferred according to the invention. The drives are disposed in the screw heads.

As a rule, the at least one hose can be constructed from any desired material and can even theoretically be produced from a metal. Preferably, however, the at least one hose consists at least in sections of a biocompatible plastic and is axially deformable. The deformability of the at least one hose causes the treatment situation to be subjected to less mechanical stress.

Preferably, the at least one bone screw contains a radiopaque material or consists of a radiopaque material. As a result, the position and location of the at least one bone screw can be determined in the body of the patient using X-ray methods. The radiopaque material can particularly preferably be selected from stainless steel, titanium, titanium alloys, tantalum, tantalum alloys, barium sulfate, plastics containing barium sulfate, zirconium oxide and plastics containing zirconium oxide.

The device according to the invention is preferably a mechanical device.

Preferably, the at least one cap can be detachably connected with the connecting element to the proximal screw head of the at least one bone screw in a fluid-tight manner or with a low leakage rate compared to the maximum possible volume flow through the at least one bone screw. The leakage rate can be regarded as low when a maximum of 10% of the volume flow exits through the at least one conduit in the at least one bone screw between the connecting element of the at least one cap and the screw head of the at least one bone screw, wherein preferably, a maximum of 1% of the volume flow exits there. Here, it is assumed that no further flow resistances occur behind the at least one fluid outlet opening. Experimentally, the leakage rate can therefore be determined by feeding a fluid through a cap and guiding it into a bone screw connected to the cap, and comparing the volume flow that exits between the cap and the screw head as a leakage flow with the volume flow that exits from the at least one fluid outlet opening.

A pharmaceutical fluid contains at least one pharmaceutical active ingredient. Solutions containing at least one antibiotic, at least one cytostatic, at least one chemotherapeutic ingredient and/or at least one antimycotic ingredient are particularly preferable. Alternative pharmaceutical fluids can contain disinfectant components. The term "pharmaceutical fluid" accordingly refers to aqueous and non-aqueous solutions and suspensions of pharmaceutical active ingredients. The term "pharmaceutical fluid" further refers to mixtures and solutions of gases in water, fluids containing water and non-aqueous fluids. The term "pharmaceutical fluid" preferably also comprises gases and gas mixtures.

It can further be provided that in the hose for feeding fluid or in the connection to a container for the pharmaceutical fluid, a valve element, in particular a return valve, is disposed which prevents a flow of the pharmaceutical fluid from the hose in the direction of the container.

In this way it is ensured that no contaminated pharmaceutical fluid can travel out of the hose into the container for the pharmaceutical fluid.

For devices according to the invention, it can also be provided that the at least one bone screw has at least one radial groove which is disposed in the surface of the screw head of the at least one bone screw and which is connected to the at least one axial groove in the screw body.

In this way, a conduit for the pharmaceutical fluid can be formed between the screw head of the bone screw and an osteosynthesis plate affixed to the bone screw. In this manner, a circuit for flushing through with the pharmaceutical fluid can be provided, said circuit in some areas running over the screw bore hold of the bone screw in the bone and thus being directly usable for medical treatment. Due to the at least one radial groove, the pharmaceutical fluid can easily flow past the screw head when the screw head is affixed to an osteosynthesis plate. The radial groove can have an axial extension in addition to a radial extension. This way, no pressure of the pharmaceutical fluid can build up within the bone that presses onto the treatment situation.

Further, it can be provided that the at least one axial groove that penetrates the outer thread of the bone screw extends from the at least one fluid outlet opening on the distal screw body through to a distal side of the screw head, wherein, preferably, the at least one axial groove extends through to the radial outer side of the screw head.

This design also aids in the formation of a circumferential conduit for the pharmaceutical fluid for the purpose of generating a flushing circuit of the pharmaceutical fluid and/or to avoid a decrease in the static pressure of the pharmaceutical fluid on the bone to be treated.

Furthermore, it can be provided that the connecting element is a protrusion on a lower side of the cap pointing to the screw head, wherein the protrusion comprises the conduit that is permeable to fluids in the at least one cap, wherein the at least one cap is reversibly inserted or insertable into the at least one conduit of the at least one bone screw with the protrusion, wherein, preferably, the protrusion is disposed in the center of the lower side of the cap, particularly preferably disposed axially along a symmetry axis of the at least one cap.

In this way, the connecting element can be connected to the at least one bone screw very easily and in a simple manner. Additionally, a fluid-directing conduit can thus be provided through the at least one cap and the at least one bone screw.

The direction description "on a lower side of the cap of the at least one cap pointing to the screw head" refers to the state in which the at least one cap with the connecting element is detachably connected to the at least one bone screw.

Here, it can be provided that the at least one cap on the lower side of the cap pointing to the screw head has a groove that extends outwards from the protrusion in the radial direction, wherein the at least one groove of the at least one cap preferably extends up to the radial edge of the at least one cap and/or a hose is connected in a fluid-permeable manner to the at least one groove of the at least one cap for discharging fluid.

The at least one groove on the lower side of the cap can be used to discharge the pharmaceutical fluid. As a result, a circuit of the pharmaceutical fluid can be provided, or at least the pharmaceutical fluid can be directed away from the bone to be treated.

It can also be provided that the at least one hose for feeding fluid is connected or connectable to a fluid reservoir in a fluid-permeable manner, wherein a pharmaceutical fluid from the fluid reservoir is pressable under pressure into the at least one hose for feeding fluid through the conduit of the at least one cap and into the at least one conduit of the at least one bone screw.

In this way, the device is further equipped and is directly usable for treatment purposes.

According to the invention, it can also be provided that, aside from being connected on the at least one fluid outlet opening, the at least one conduit in the screw body is not connected to the at least one axial groove in the screw body.

This ensures that the pharmaceutical fluid exits at the at least one fluid outlet opening on the distal screw end and is thus fully available there for treatment. In particular, flushing with the pharmaceutical fluid is also conducted in the region of the at least one fluid outlet opening on the distal screw end.

Furthermore, it can be provided that the at least one cap is formed as a cupola with an underside that is planar with the exception of the connecting element and/or that the at least one cap fully covers the screw head, the at least one cap preferably overlapping the screw head.

It can also be provided that the at least one cap has a diameter that is at least the same size as the outer diameter of the screw head.

These measures serve to enable a well sealable connection between the at least one cap and the screw head of the at least one bone screw over the largest area possible. The cupola form ensures that no injuries to the covering soft tissue occur as a result of sharp edges. Due to the coverage of the at least one bone screw with the at least one cap, the respective cap can be designed with such a size that the cap only has gradually rising edges, as a result of which the covering soft tissue is protected.

Preferably, it can also be provided that the at least one cap has one opening or multiple openings for discharging fluids, which are connectable or connected to a hose for discharging fluid, wherein the opening or the openings is or are preferably disposed on a lower side of the cap of the at least one cap pointing towards the screw head.

In this way, the at least one cap can be used to create the circuit of the pharmaceutical fluid. Due to the opening or several openings for discharging fluids, the pharmaceutical fluids can be directed out of the region of the screw head with a hose for discharging the pharmaceutical fluid. Unwanted local collection of pharmaceutical fluid above and alongside the cap is thus effectively prevented. With this design variant, a continuous flushing of the bore conduit of the bone screw and the adjacent bone tissue with pharmaceutical fluids, specifically with antibiotic solutions, is possible. Due to the arrangement of the opening or of the multiple openings on the lower side of the cap of the at least one cap, the pharmaceutical fluids are discharged directly after exiting on the screw head.

Here, it can be provided that the at least one hose for feeding fluid and the hose for discharging fluid are interconnected in the longitudinal direction; preferably, they are interconnected parallel adjacent to each other or are disposed coaxially in relation to each other.

This makes handling easier. Additionally, space-saving introduction and removal of pharmaceutical fluids is thus possible.

According to a further design of the present invention, it can be provided that the device has at least one osteosynthesis plate. It can also be provided that the at least one cap has at least one latching element with which the at least one cap can be engaged with an osteosynthesis plate, wherein preferably, the at least one latching element is disposed on a lower side of the cap of the at least one cap pointing towards the screw head.

In this way, the at least one cap can be used to secure the bone screw on the osteosynthesis plate. Due to the latching element, the at least one cap can be reversibly affixed on the osteosynthesis plate in order to prevent unintentional sliding out of the connecting element from the at least one conduit of the at least one bone screw.

According to the invention, it can be provided that the device has at least one osteosynthesis plate. Here, it can be provided that the osteosynthesis plate has multiple holes, preferably multiple holes with a diameter that is smaller than the screw head of the at least one bone screw and larger than the outer diameter of the outer thread of the at least one bone screw. In this way, the device can also be used to immobilize a fracture.

Furthermore, it can be provided that the at least one hose for feeding fluid has a maximum radial expansion of 5 percent, in particular, a maximum radial expansion of 1 percent, with an inner pressure of 5 bar, wherein, preferably, a hose for discharging fluid also has a maximum radial expansion of 5 percent, in particular a maximum radial expansion of 1 percent, with an inner pressure of 5 bar.

This ensures that the hose or hoses do not expand excessively while the pharmaceutical fluid is being pressed in, and then exert an elastic pressure on the bone to be treated via the pharmaceutical fluid within. Additionally, as a result, a subsequent flow or backflow of the pharmaceutical fluid is avoided when the pressure for driving the fluid flow is reduced or withdrawn. These measures prevent excessive pressure building up in the marrow area during the application of pharmaceutical fluids, which could lead to embolisms. This further guarantees that while pharmaceutical fluids are being pressed into the at least one hose for feeding fluid and in some cases also during the fluid return flow through the hose for discharging fluid, almost no radial expansion of the hoses occurs. This way, pain in the infected or inflamed tissue can be avoided during the application of the pharmaceutical fluids.

Further, it can be provided that the at least one cap is at least two caps, and the at least one bone screw is at least two bone screws, wherein the at least two caps are affixed with their connecting elements in two different bone screws of the at least two bone screws, wherein the at least two caps are interconnected via one tube or two tubes in a fluid-permeable manner.

It can hereby also be provided that the at least one hose for feeding fluid is only connected to one of the at least two caps, wherein the pharmaceutical fluid is distributable over the at least two bone screws via the at least two caps that are interconnected via the one tube or the two tubes, or the at least one hose for feeding fluid and a hose for discharging fluid are only connected to one of the at least two caps in a fluid-permeable manner, wherein the pharmaceutical fluid is serially directable through the at least two bone screws via the at least two caps that are interconnected via the one tube or the two tubes.

As a result, several bone screws can be jointly used for flushing with the pharmaceutical fluid via a shared connection.

It is also possible to use coaxial tubes, so that fluid can be removed via just one of the at least two caps and a hose connected thereto for discharging the pharmaceutical fluid. The tube or tubes can be inserted into each other in the manner of a telescope and such that they can be moved against each other. It is also possible to house the at least two caps and the tube or tubes in a flat, strip-shaped plastic body.

According to the invention, it can be provided that one of the at least two caps is inserted respectively in the at least two bone screws, wherein the caps are interconnected via two elastic tubes in a fluid-permeable manner, wherein the hose for feeding the pharmaceutical fluid and the hose for discharging the pharmaceutical fluid are connected with just one cap respectively in a fluid-permeable manner, so that pharmaceutical fluid is distributable over the at least two bone screws via the interconnected caps, and the pharmaceutical fluid flowing back can be discharged via the hose for discharging the pharmaceutical fluid.

It can also be provided that the device has a container for the pharmaceutical fluid, wherein preferably the container is a hollow cylinder with a piston that is axially movable in the hollow cylinder, which closes a first end of the hollow cylinder, wherein the hollow cylinder has a delivery opening on an end positioned opposite the first end, which is connected or connectable to the at least one hose for feeding fluid, particularly preferably, is connected or connectable to the at least one hose via a manually operable valve element for regulating the flow speed of the pharmaceutical fluid.

As a result, the device can simultaneously be used to create a volume flow of the pharmaceutical fluid. Furthermore, no separate reservoir for the pharmaceutical fluid needs to be connected to the device. Preferably, the piston is drivable with at least one tensioned elastic spring.

Furthermore, it can be provided that the container contains a pharmaceutical fluid, in particular containing at least one antibiotic active ingredient, at least one antimycotic active ingredient and/or at least one chemotherapeutic ingredient.

Due to this, the device can be directly used for treatment purposes.

According to a preferred further development of the present invention, it can be provided that the device has a conveyor apparatus with which the pharmaceutical fluid is pressable out of a container that is connected or connectable to the conveyor apparatus, into at least one hose for the fluid feed, through the conduit in the at least one cap, through the at least one conduit in the screw body of the at least one bone screw, and through the at least one fluid outlet opening into the surrounding area of the at least one bone screw, wherein, preferably, the conveyor apparatus has an energy storage element, in particular at least one tensioned spring, wherein the conveyor apparatus is drivable with energy from the energy storage element, wherein particularly preferably, with the energy storage element, a piston in a hollow cylinder is to be driven as the container in the direction of an opposite delivery opening.

With a conveyor apparatus, the device can be directly used to create a volume flow of the pharmaceutical fluid. If the conveyor apparatus comprises an energy storage element, the device does not need to be connected to an external energy supply in order to drive the conveyor apparatus. A tensioned spring contains sufficient energy to press out a quantity of between several milliliters and several centiliters of the pharmaceutical fluid with the device.

Furthermore, it can be provided that the device has at least one locking cap with which the at least one conduit is reversibly lockable in the screw body of the bone screw, wherein, preferably, the at least one locking cap has a proximal pin with which the at least one conduit is reversibly lockable up to at least one fluid outlet opening.

It is advantageous when before and during implantation, the at least one conduit of the bone screw and a hollow space in the screw head (as a part of the at least one conduit in the screw body) is filled out with a pin that can be manually removed and that comprises a locking cap.

Such measures prevent the at least one conduit in the bone screw from being clogged by particles such as bone splinters. After the bone screw has been screwed in, the pin is removed and the at least one conduit in the bone screw is opened up.

The portion of the connecting element of the at least one locking cap, which protrudes over the upper edge, can preferably be designed as an external hex. This makes it possible to screw the at least one bone screw into the bore hole with an external hex (Allen key). The prerequisite for this is that the connecting element and the external hex are made of a mechanically stable material such as steel, so that when screwing in, no torsion of the connecting element and the hex occurs.

Further, it can be provided according to the invention that the portion of the at least one locking cap, which protrudes over the upper edge, is formed as a handle. This makes it possible to screw the bone screws into the pre-drilled bore hole with the handle and the connector. The precondition for this is, however, that the connector and the handle are either made from a high-strength plastic or from metal in order to have sufficient torsional stability.

The invention is based on the surprising finding that as a result of the conduits in the at least one bone screw and in the at least one cap, and due to the at least one axial groove, it is possible to supply the surrounding area of the bone screw and thus the bone to be treated with the device with a pharmaceutical fluid, or to flush or rinse around it and thus to make it accessible for an adjustable treatment. Through a continuation of the axial groove through to the radial edge of the screw head, the surfaces of the bone and of the osteosynthesis device are also made accessible for the pharmaceutical fluid.

As an application and flushing system, the device according to the invention enables a local application and flushing with pharmaceutical fluids with at least partial soft tissue coverage over a period of several days to weeks. For this purpose, within the scope of the present invention, commonly used bone screws such as cancellous and cortical screws are modified such that pharmaceutical fluids such as aqueous antiseptic or antibiotic solutions can be introduced via the bone screws through to the medulla, and that simultaneously, the drill channels of the bone screws and the outer side of the bone screws can be rinsed around with the pharmaceutical fluids, at least in part.

The device or the application and flushing system is designed such that, following completion of the delivery of pharmaceutical fluids, the modified bone screws can remain in the bone tissue in the same way as commonly used bone screws, if this is medically required. For this purpose, parts of the device that serve to introduce the pharmaceutical fluids are removable from the bone screws in a simple manner.

With the application system according to the invention, or with the device according to the invention, pharmaceutical fluids can be introduced through the hose and through the at least one cap into the at least one conduit of the bone screw after the at least one bone screw has been screwed into the bone tissue. The pharmaceutical fluid then flows out of the at least one fluid outlet opening in the region of the distal end of the bone screw and can thus reach the surrounding bone tissue. When sufficient fluid from the at least one fluid outlet opening flows after it, the pharmaceutical fluid migrates in the direction of the screw head via the at least one axial groove. Due to the fact that the axial groove lies deeper in the direction of the screw longitudinal axis than the base of the thread of the bone screw, a flow in the direction of the screw head can be guaranteed. The adjacent bone tissue can thus not close the groove base. The surrounding bone tissue is moistened by the pharmaceutical fluid as a result. The pharmaceutical fluid can then exit out of the drill channel in the bone past the radial grooves on the lower side of the screw head. The formation of an overpressure in the bone tissue, specifically in the medulla, resulting from the fluid having been pressed in, is thus effectively prevented. The pharmaceutical fluid can be effective in the adjacent bone tissue as well as on the surface of the bone screw.

The particular advantage of the application and flushing device according to the invention is that a local application of pharmaceutical fluids, particularly of antibiotic solutions of any composition required, can be conducted with simultaneous stabilization of the fractured bone. Bore holes in the bone tissue for additional screws or pins, as are required when external fixators are used, are not necessary. An application of pharmaceutical fluids is possible for a period of hours to several days. Following completion of the fluid application, only the at least one cap with the hose is removed or drawn out of the at least one bone screw. The at least one bone screw can then remain in the bone tissue for the stabilization of the fracture.

The subject of the invention is in particular a medical device for the temporary, local application of and flushing with pharmaceutical fluids or other medical fluids over a period of one day to several weeks. The device according to the invention is above all intended for the prevention and also for the treatment of periprosthetic infections of screw and plate osteosyntheses, and for the mechanical stabilization of fractures. The device according to the invention is provided and suitable as an application and flushing system for local applications of pharmaceutical fluids in and on bone tissue over a period of several days to weeks.

An exemplary device according to the invention for the local application and/or for flushing for pharmaceutical fluids consists of:
a) at least one bone screw with an outer thread and a proximal screw head, with at least one axial, fluid-permeable conduit in the screw body, which begins at the screw head, and with at least one fluid outlet opening connected to the conduit on the distal screw end,
b) at least one axial groove penetrating the outer thread of the bone screw which extends from the fluid outlet opening on the outer screw body through to the lower side of the screw head, wherein the base of the groove is deeper in the direction of the longitudinal axis than the base of the thread,
c) a screw head that has one or multiple radial grooves on its lower side, which are connected to the at least one axial groove of the screw body,
d) a cap with a pin (as a connecting element) on the lower side of the cap, wherein the pin has a conduit that is permeable for fluids, which is connected or connectable in a fluid-permeable manner to a conduit in the cap, which opens out on an outer side of the cap into an inlet opening, wherein the cap with the pin is reversibly inserted or insertable into the conduit of the bone screw, and
e) a first hose for feeding fluid, which is connected in a fluid-permeable manner with the inlet opening of the cap, and wherein the hose is connectable in a fluid-permeable manner with a fluid reservoir, with which the fluid can be pressed under pressure into the hose through the conduit of the cap and the conduit of the bone screw.

A further example is a device according to the invention for pressing out pharmaceutical fluids with a local application and flushing system, which consists of:
a) at least one bone screw with an outer thread and a proximal screw head, with at least one axial, fluid-permeable conduit in the screw body, which begins at the screw head, and with at least one fluid outlet opening connected to the conduit on the distal screw end,
b) at least one axial groove penetrating the outer thread of the bone screw which extends from the fluid outlet opening on the outer screw body through to the lower side of the screw head, wherein the base of the groove is deeper in the direction of the longitudinal axis than the base of the thread,
c) a screw head that has one or multiple radial grooves on its lower side, which are connected to the at least one axial groove of the screw head,
d) a cap with a pin (as a connecting element) on the lower side of the cap, wherein the pin has a conduit that is permeable for fluids, which is connected or connectable in a fluid-permeable manner to a conduit in the cap, which opens out on an outer side of the cap into an inlet opening, wherein the cap with the pin is reversibly inserted or insertable into the conduit of the bone screw, and
e) a first hose for feeding fluid, which is connected to the inlet opening of the cap in a fluid-permeable manner,
f) wherein the first hose is connected in a fluid-permeable manner with a pressing out device, wherein the pressing out device consists of:
f1) a hollow cylinder containing a pharmaceutical fluid,
f2) a piston that is axially movable in the hollow cylinder, which closes one end of the hollow cylinder,
f3) at least one fluid-permeable delivery opening in the closed head of the hollow cylinder,
f4) a valve element, and
f5) a spring element that is connected to the axially movable piston, wherein with the tensioned spring element, the piston is movable in the direction of the delivery opening, so that the pharmaceutical fluid in the hollow cylinder can be pressed into the hose end of the first hose through the delivery opening and the valve element.

Due to this exemplary device according to the invention, it is possible to continuously apply pharmaceutical fluids over a period of hours up to several days without electrically driven pump systems being required. The device can be made from plastic such that it can be carried by mobilized patients.

It is to be understood that both the foregoing general description and the following detailed description are exemplary, but are not restrictive, of the disclosure.

BRIEF DESCRIPTION OF THE DRAWING

In the following, further exemplary embodiments of the invention will be explained with reference to twelve schematic figures, though without thereby limiting the invention. Included in the drawing are the following figures.

DETAILED DESCRIPTION OF THE DISCLOSURE

Figure 1:
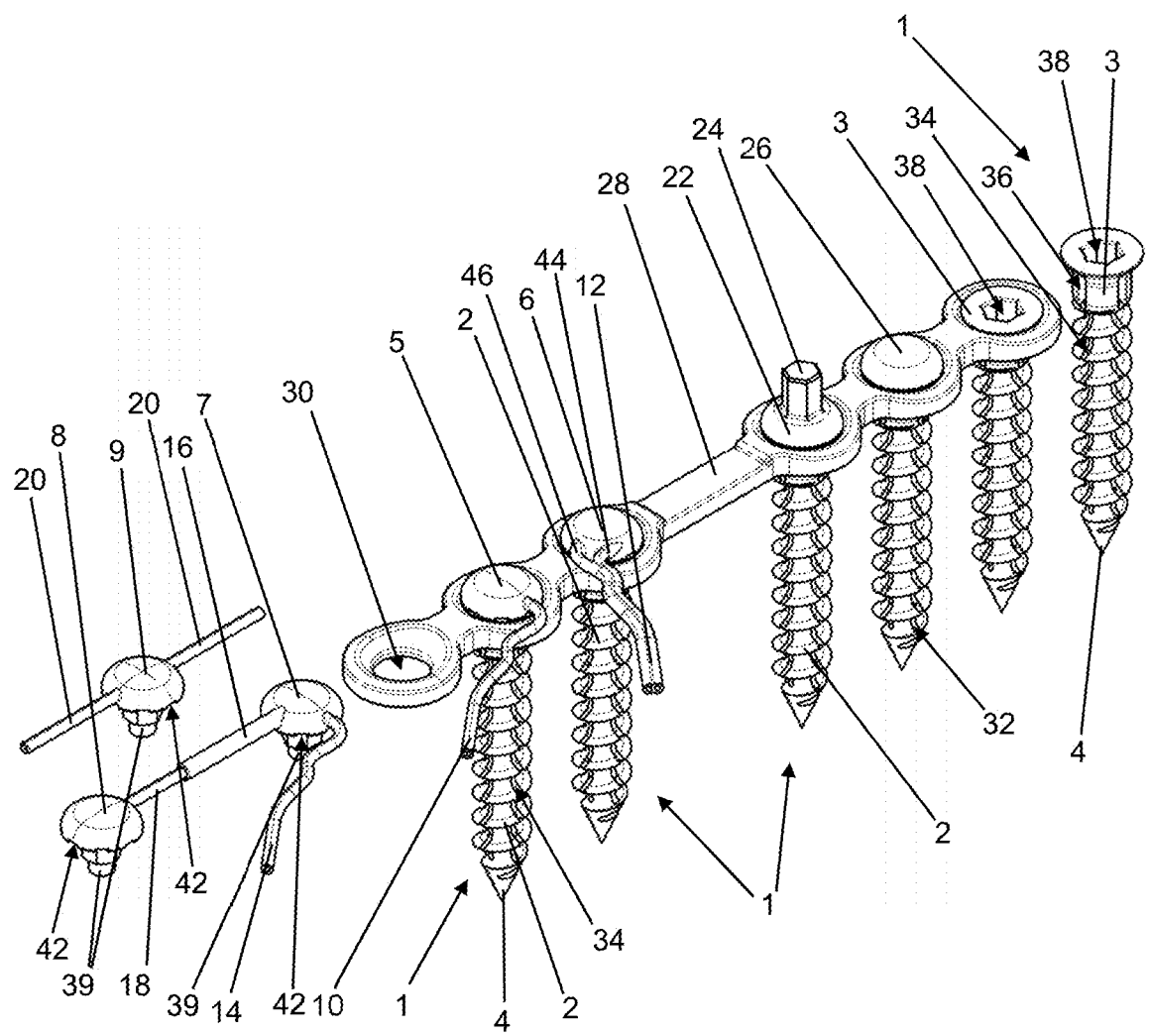
FIG. 1 shows a schematic perspective view of a proximal side of an exemplary first device according to the invention for the local application and flushing of pharmaceutical fluids.
Figure 2:
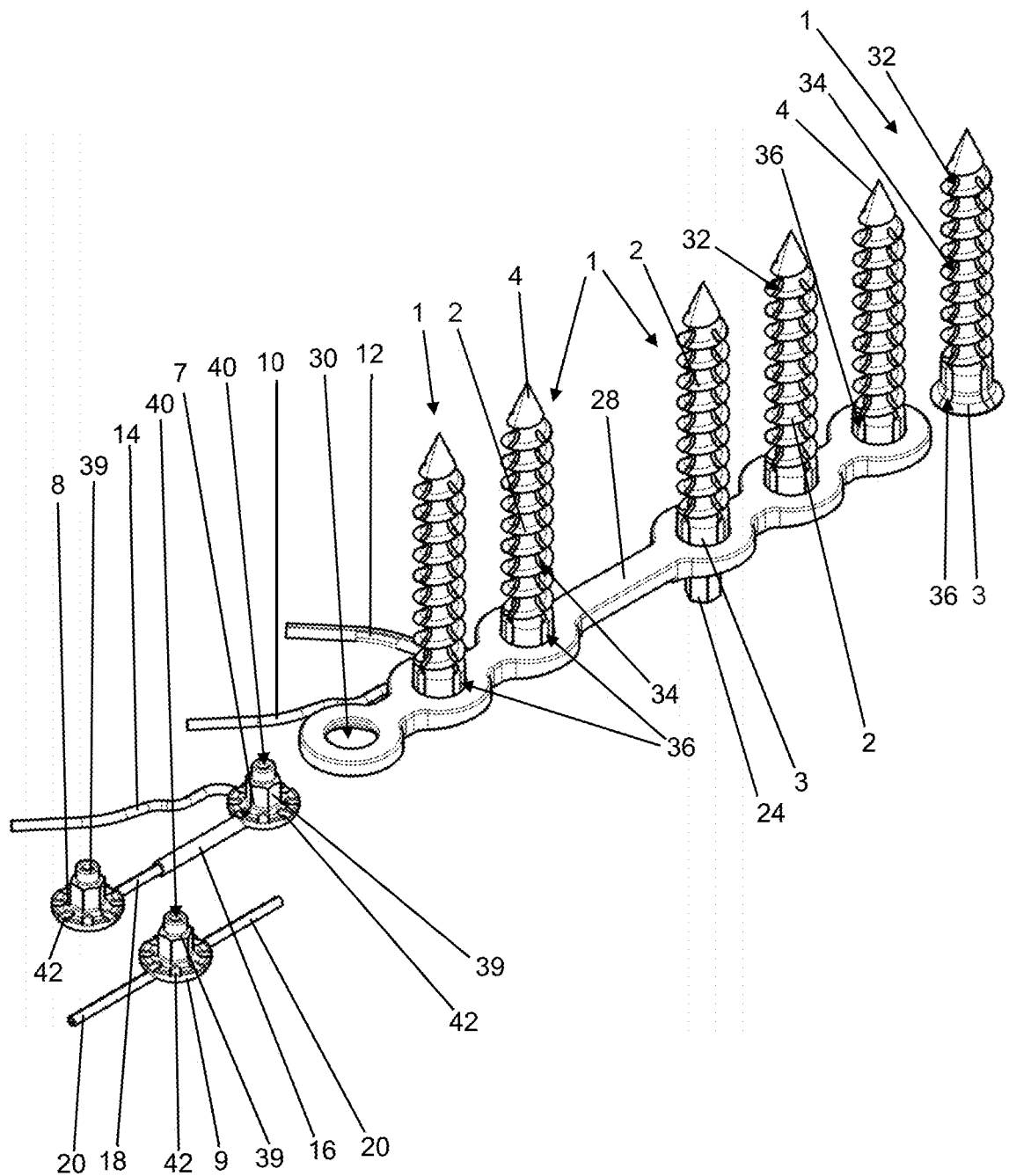
FIG. 2 shows a schematic perspective view of a distal side of the device according to FIG. 1.
Figure 3:
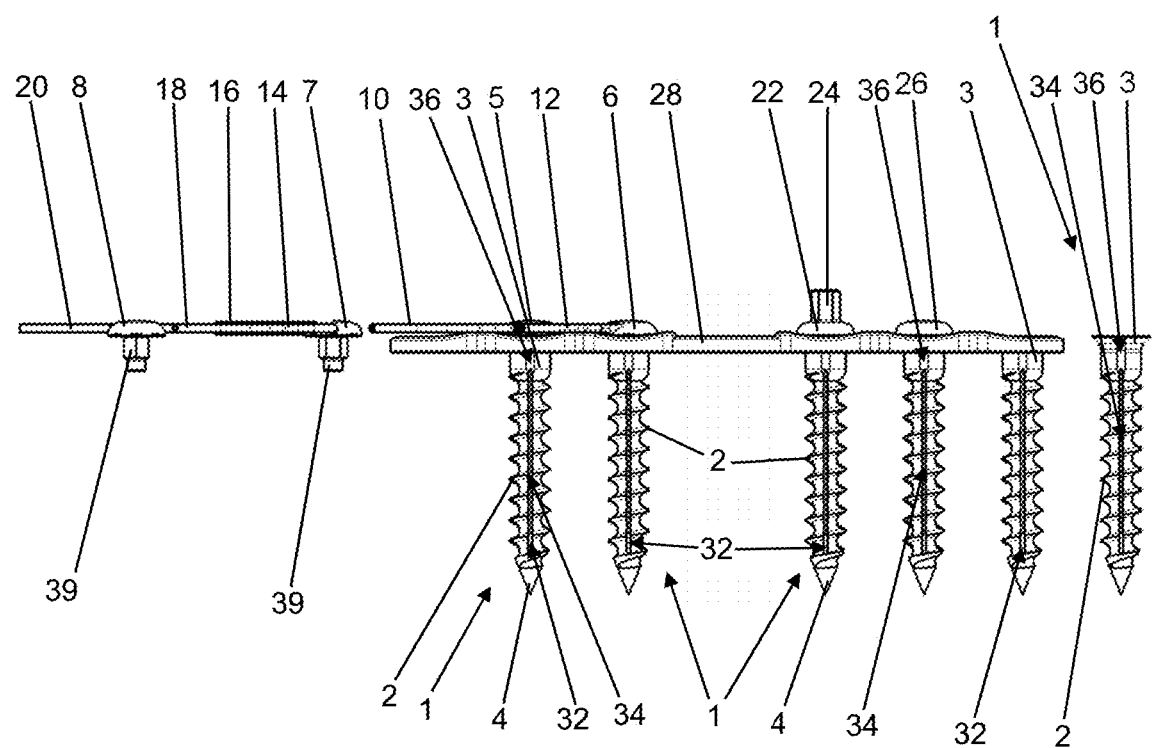
FIG. 3 shows a schematic side view of the device according to FIGS. 1 and 2.

In the figures and in the description below related to the exemplary embodiments of the present invention explained with reference to the figures, the same reference numerals are used for the same or similar parts, in some cases for different exemplary embodiments and different individual parts, in order to make it easier to compare the exemplary embodiments, and for the sake of clarity.

Figure 4:
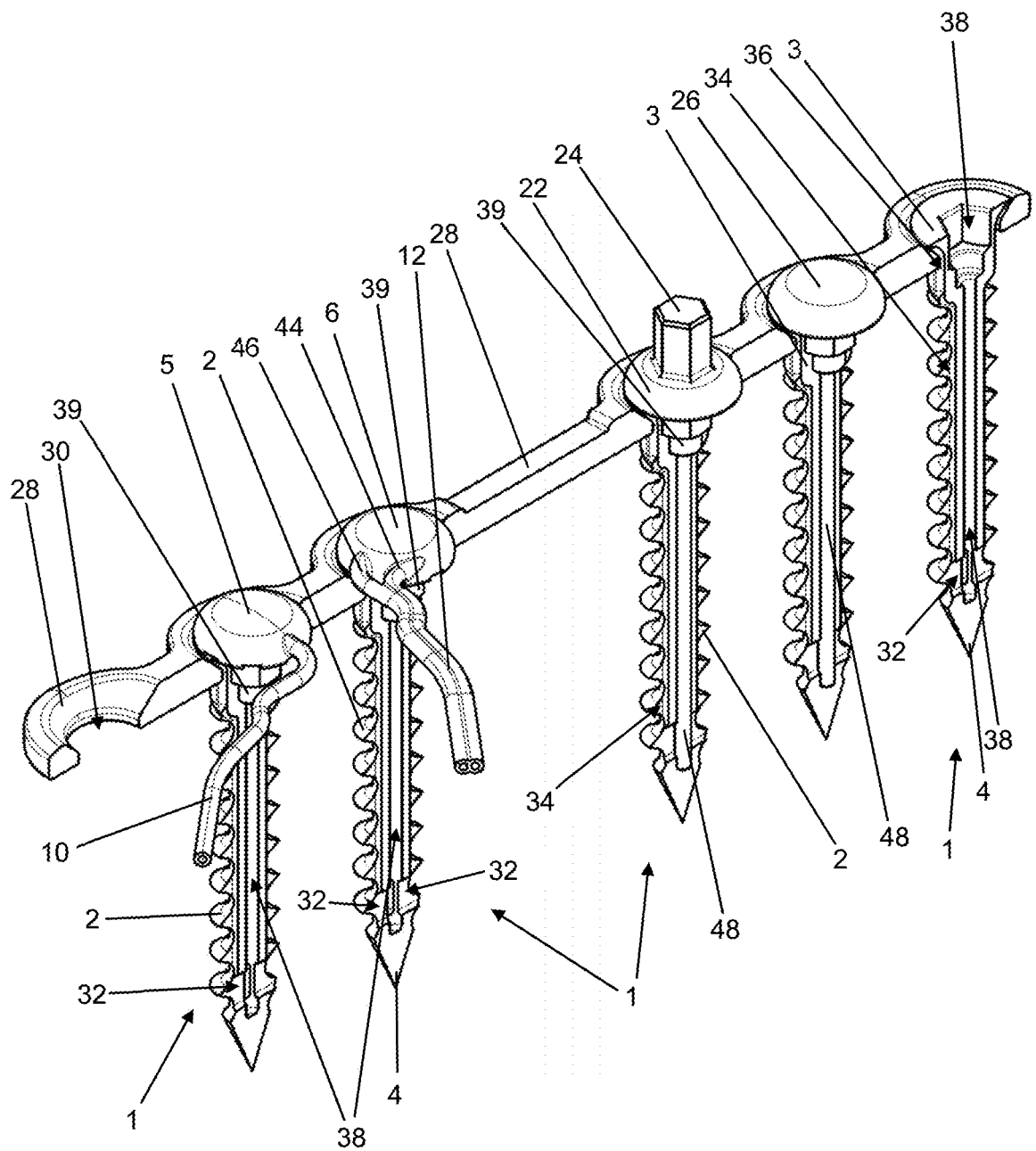
FIG. 4 shows a schematic perspective partial view of a proximal side of parts of an exemplary second device according to the invention for the local application and flushing of pharmaceutical fluids.
Figure 5:
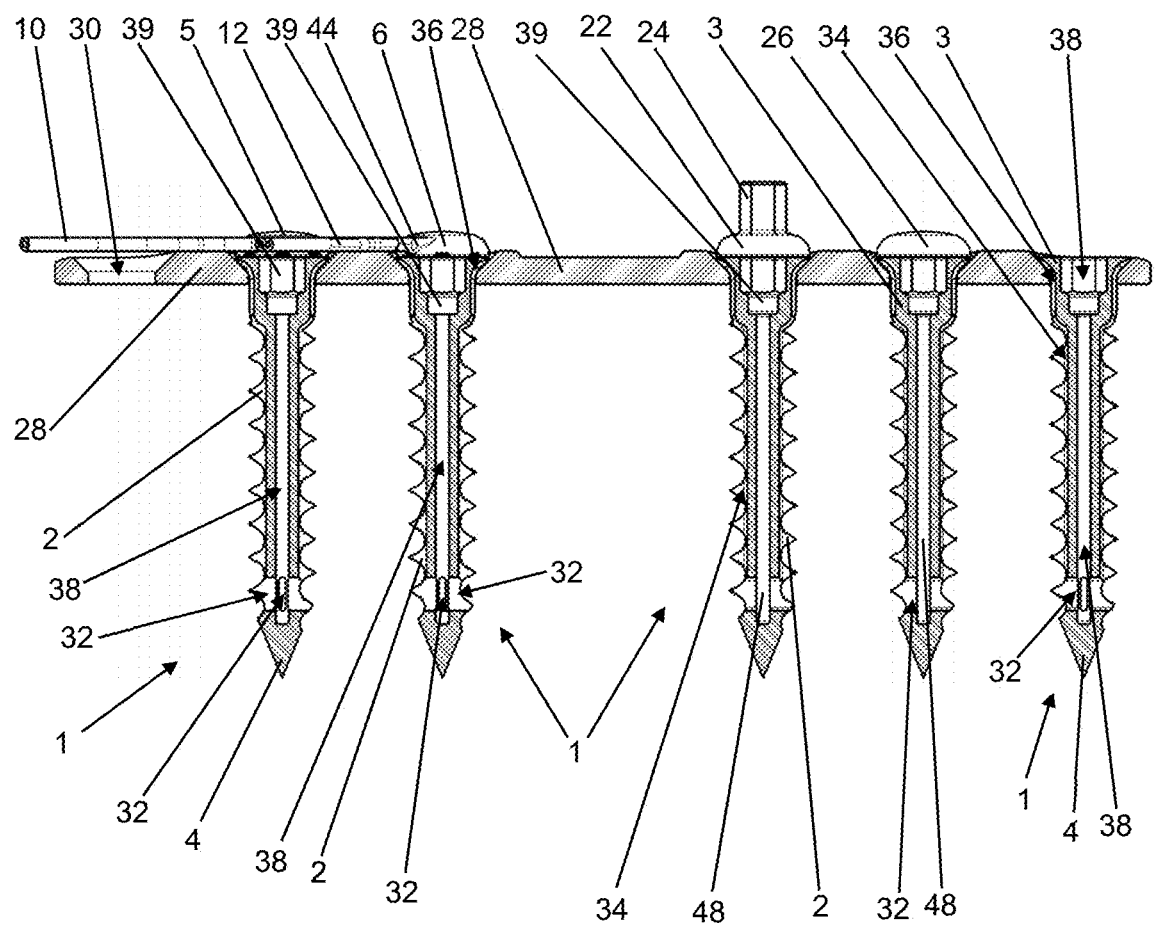
FIG. 5 shows a schematic side partial view of the parts according to FIG. 4.
Figure 6:
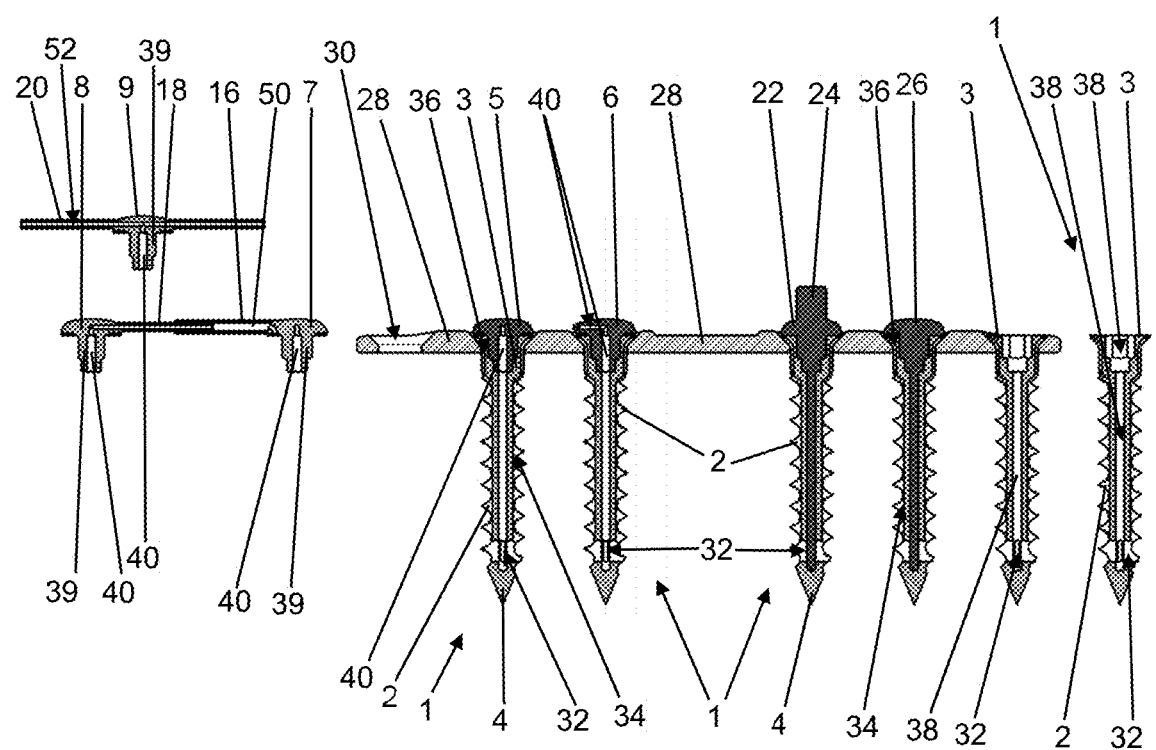
FIG. 6 shows a schematic side cross-sectional view through of the first device according to the invention according to FIGS. 1 and 3.

FIGS. 1 to 3 and 6 to 8 show a first exemplary device according to the invention and its parts in different depictions. FIGS. 4 and 5 show a second exemplary device according to the invention in different depictions. FIGS. 9 to 12 show schematic depictions of a conveyor apparatus, which can be a part of a device according to the invention.

Figure 7:
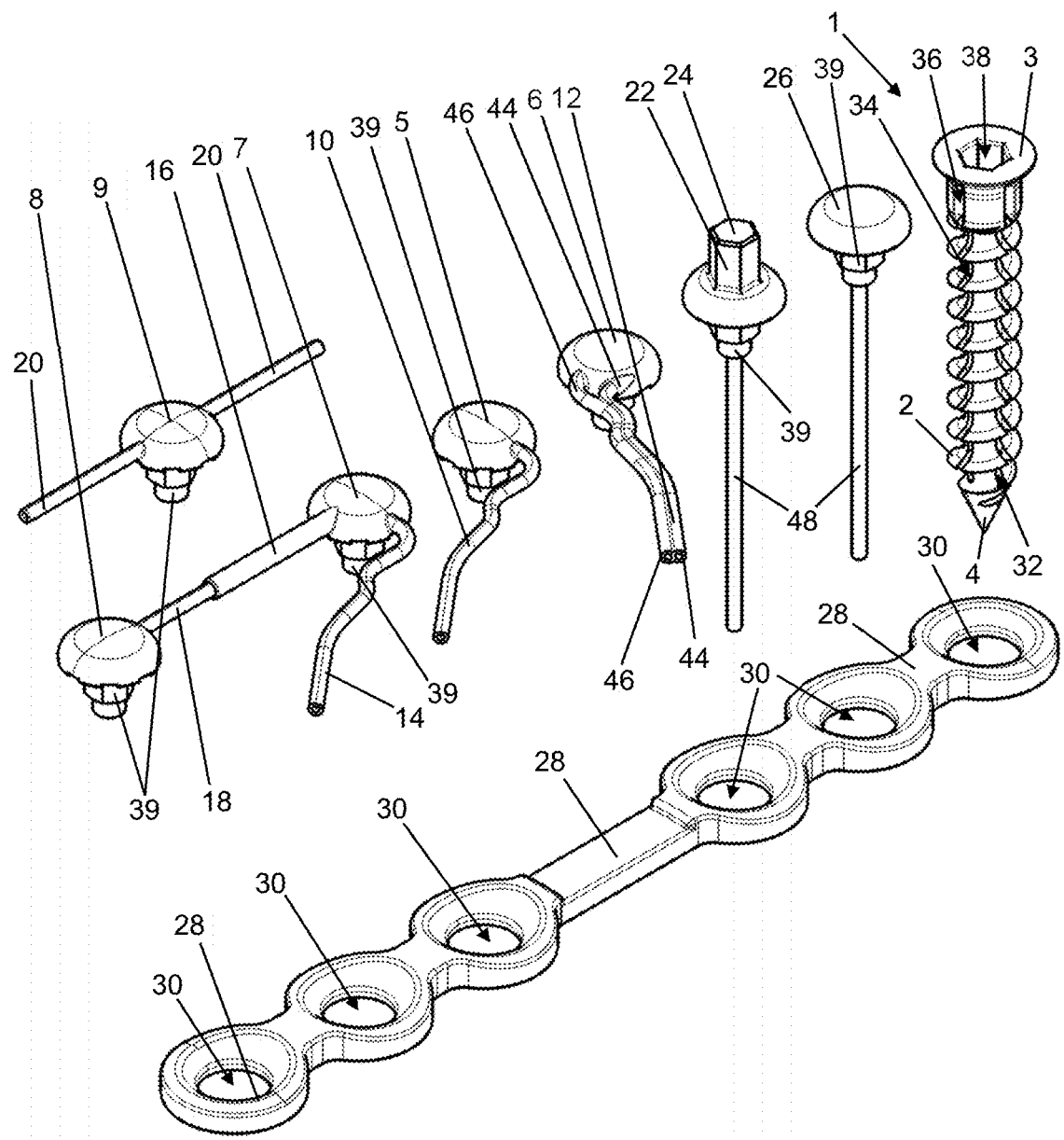
FIG. 7 shows a schematic perspective view of a proximal side of all individual parts of the first exemplary device according to the invention, separated from each other.
Figure 8:
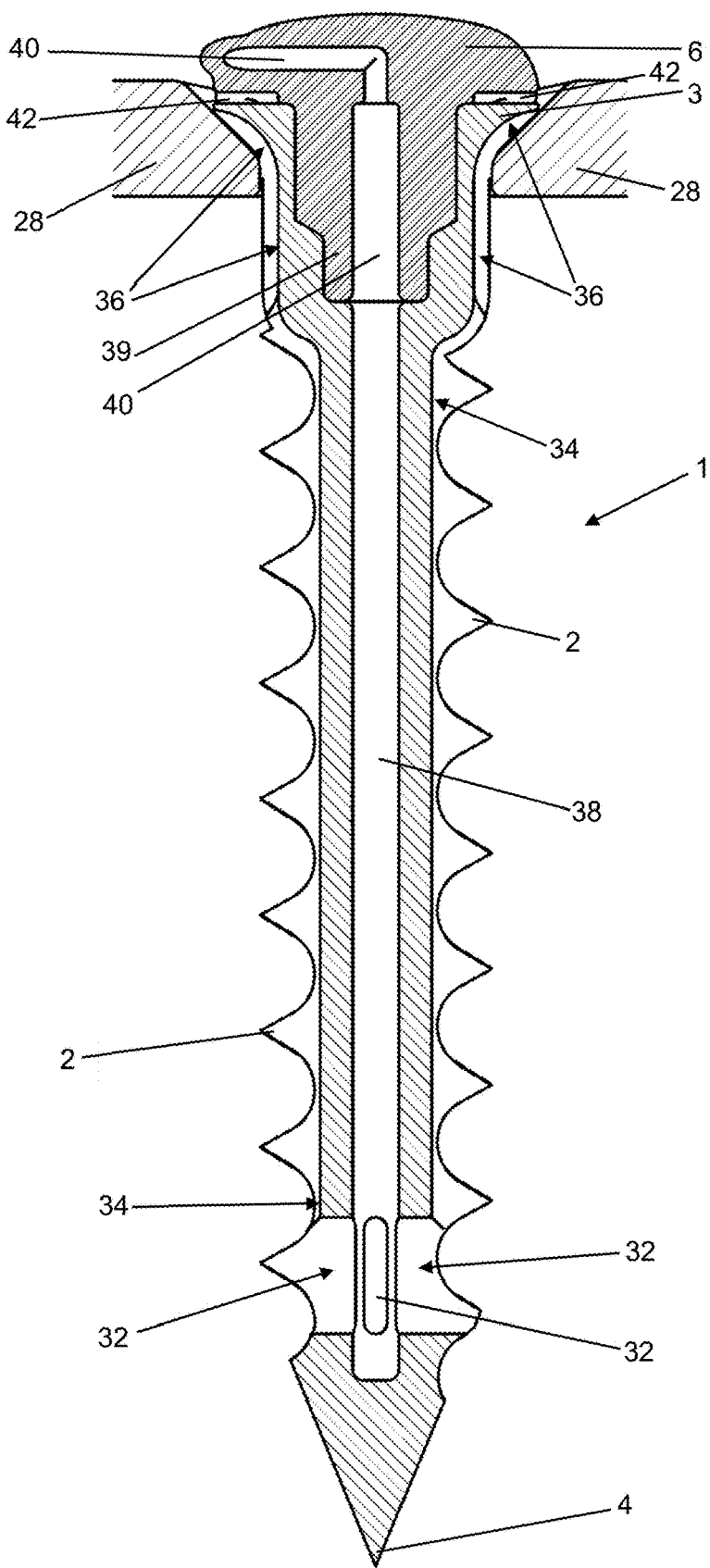
FIG. 8 shows a schematic detailed view as a sectional enlargement of FIG. 6.
Figure 9:
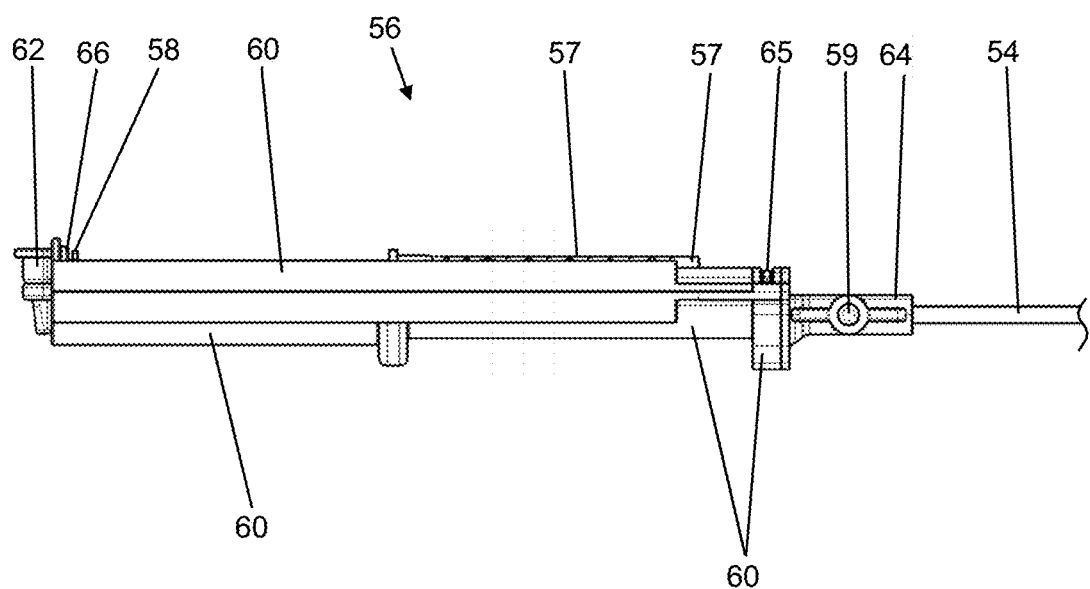
FIG. 9 shows a schematic side view of a conveyor apparatus to be disposed proximally, containing a container for connection with a device according to the invention.
Figure 10:
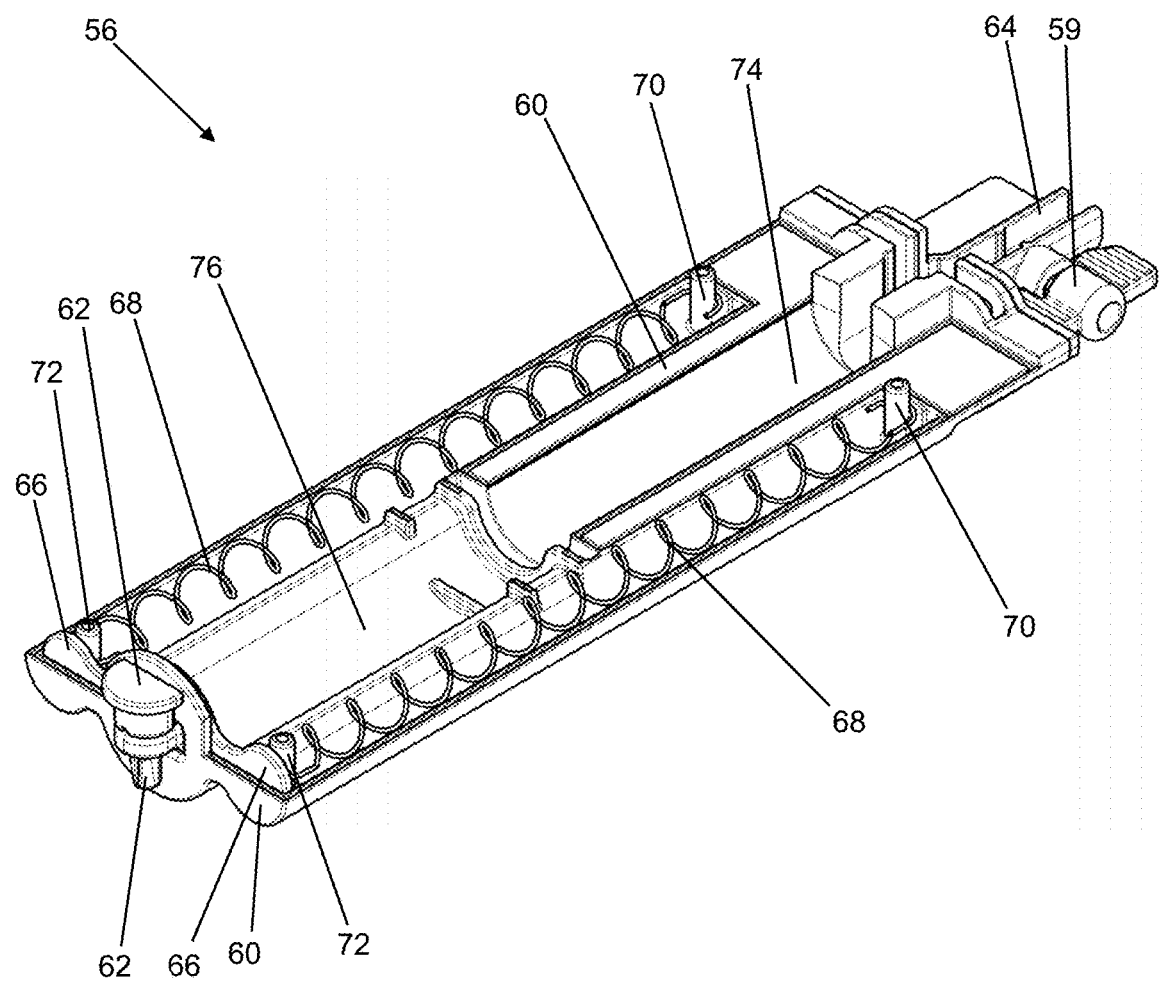
FIG. 10 shows a schematic perspective partial view of the conveyor apparatus according to the invention according to FIG. 9.
Figure 11:
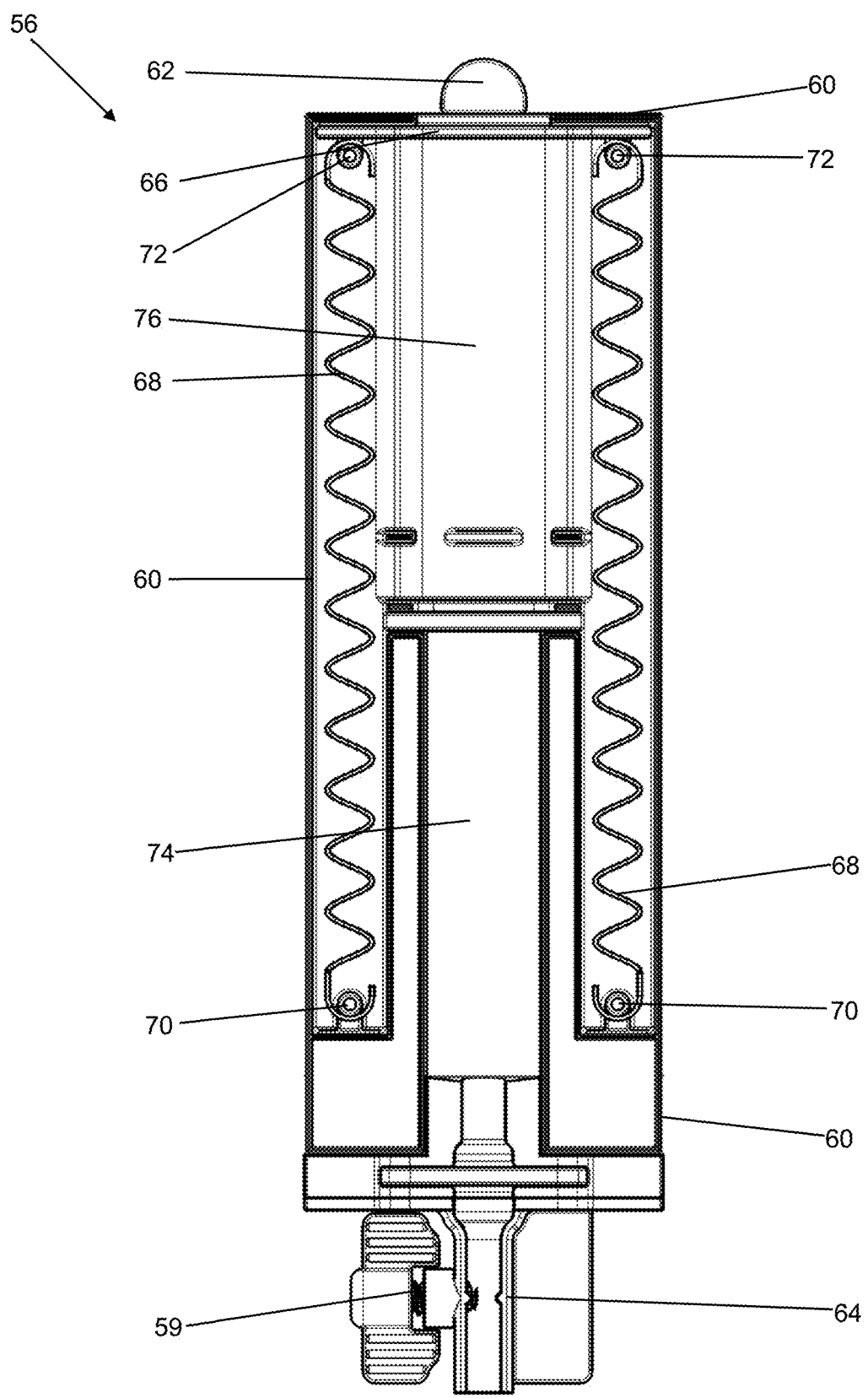
FIG. 11 shows a schematic partial top view of the conveyor apparatus according to FIG. 10 in a tensioned state.
Figure 12:
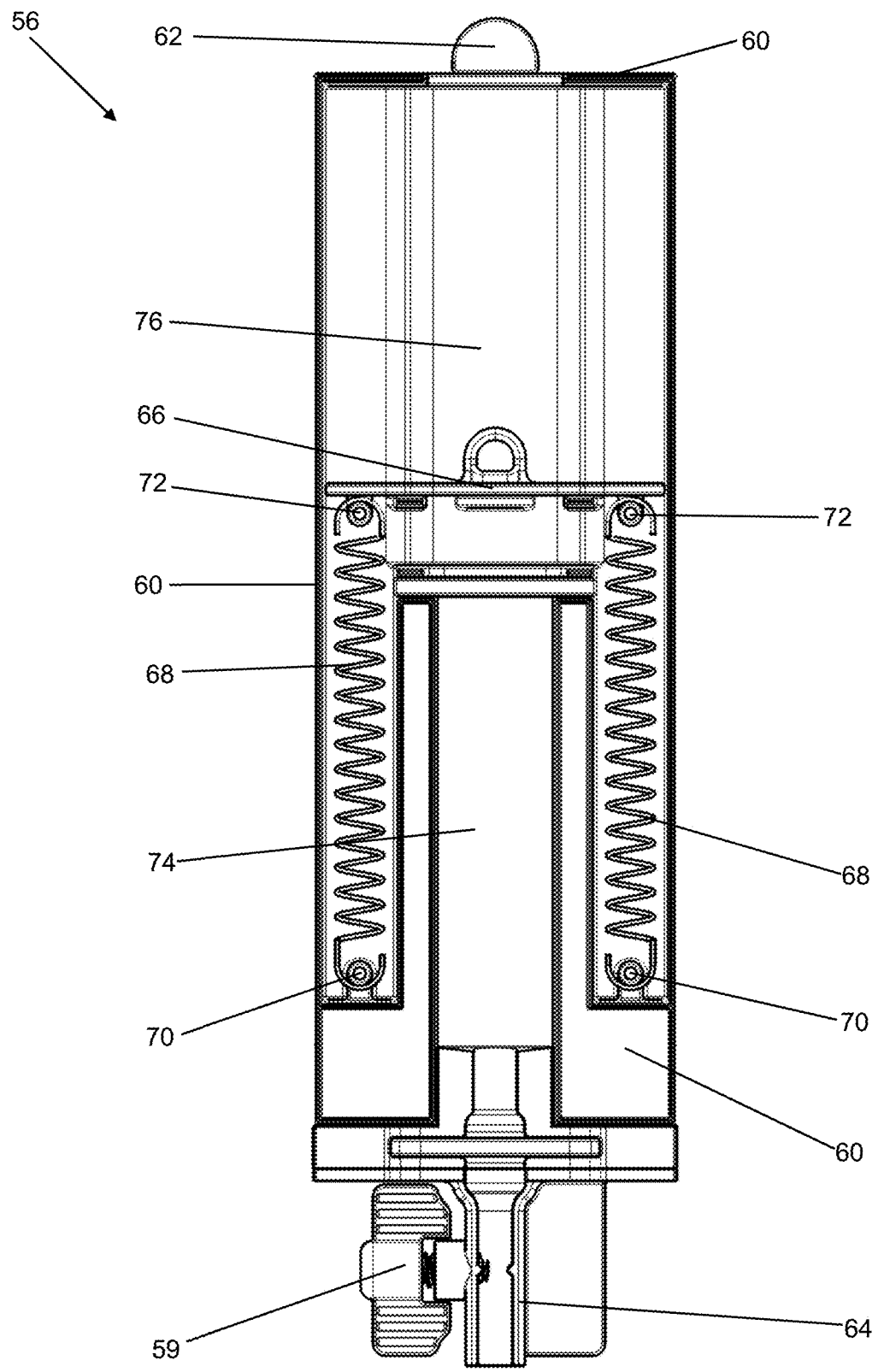
FIG. 12 shows a schematic partial view of the conveyor apparatus according to FIG. 10 in a relaxed state.

The first exemplary device according to the invention, which is shown in FIGS. 1 to 3 and 6 to 8, and the second exemplary device according to the invention, which is shown in FIGS. 4 and 5, can comprise a plurality of bone screws 1. FIGS. 1, 2, 3 and 6 respectively show six bone screws 1, FIGS. 4 and 5 respectively show five, and FIG. 7 shows one of the bone screws 1. The bone screws 1 can each have the same construction and can consist of a metal such as titanium or another biocompatible metal, of which a screw body of the bone screws 1 consists. The screw body here comprises the entire bone screw 1.

The bone screws 1 have an outer thread 2, with which the bone screws 1 can be screwed into a bone (not shown). For this purpose, the outer thread 2 can be self-cutting. On a proximal end of the bone screws 1 (above in FIGS. 1 and 3 to 8 and below in FIG. 2), the bone screws 1 end in a screw head 3. On a distal screw end 4 of the bone screw 1 opposite the screw head 3 (below in FIGS. 1 and 3 to 8 and above in FIG. 2), the bone screws 1 can be conically tapered.

The devices according to the invention can have several different caps 5, 6, 7, 8, 9, with which the bone screws 1 can be closed or covered on the screw head 3. For this purpose, it can be provided that the different caps 5, 6, 7, 8, 9 are affixed on a proximal side of the screw head 3. The caps 5, 6 are shown in FIGS. 1 to 8 in a state of being detachably connected to the screw heads 3 of two bone screws 1, while the caps 7, 8, 9 are shown as being not connected to screw heads 3 of bone screws 1. The caps 5, 6, 7, 8, 9 shown present different possible designs. It is clear that a device according to the invention can have only individual caps 5, 6, 7, 8, 9, or multiple caps 5, 6, 7, 8, 9 of just one of the different types, or any combination required of the caps 5, 6, 7, 8, 9 shown or caps adapted from them. Any selection required can therefore be used to realize the present invention of caps 5, 6, 7, 8, 9 that are suitable for implementing the present invention. Each of the caps 5, 6, 7, 8, 9 has a side inlet opening through which the pharmaceutical fluid can be introduced into the cap 5, 6, 7, 8, 9.

The caps 5, 6, 7, 8, 9 shown in FIGS. 1 to 8 differ from each other in terms of their different possibilities for directing through pharmaceutical fluids. On the cap 5, a hose 10 for feeding fluid can be connected to the inlet opening of the cap 5. On the cap 6, a double hose 12 can be connected at the side which comprises a hose 44 for discharging fluid and a hose 46 for feeding fluid, wherein the hose 46 for feeding fluid is connected to the inlet opening of the cap 6. The cap 7 can be connected at the side to a hose 14 for feeding fluid which is connected to the inlet opening of the cap 7. In addition, the cap 7 can be connected to the cap 8 via two tubes 16, 18 that are inserted into each other in a telescopic manner. For this purpose, a tube 16 with a larger diameter can be affixed at the side to the cap 7, while on the cap 8, a tube 18 with a smaller diameter can be affixed at the side, wherein the tube 18 is connected to the inlet opening of the cap 8. The outer diameter of the tube 18 can correspond to the inner diameter of the tube 16, so that the distance between the cap 7 and the cap 8 is adjustable and the two tubes 16, 18 that are telescopically connected provide a connection for directing through the pharmaceutical fluid between the two caps 7 and 8. The cap 9 can be connected on two opposite sides via one tube 20 respectively (one for feeding fluid, one for discharging fluid) to a reservoir of the pharmaceutical fluid (not shown, however, see, e.g., FIG. 9), or it can be connected to other similar caps 9 or to other caps 5, 6, 7, 8. For this purpose, one of the tubes 20 is connected to the inlet opening of the cap 9 and the respective other tube 20 for discharging fluid. In this manner, a plurality of identical or different caps 5, 6, 7, 8, 9 can be together connected to a reservoir for the pharmaceutical fluid (see, e.g., FIG. 9), either serially or also in parallel. The pharmaceutical fluid can then preferably flow through the caps 5, 6, 7, 8, 9 and through the connected bone screws 1 and particularly preferably, can also be discharged out of these again.

In order to keep the bone screws 1 locked and possibly also to enable them to be screwed into a bone more easily, a locking cap 22 can be inserted into the bone screws 1 with a proximal external hex 24 or a locking cap 26 with a flat cover. The locking caps 22, 26 serve above all to seal the bone screws 1 when none of the caps 5, 6, 7, 8, 9 is affixed to the bone screw 1.

The device can have an osteosynthesis plate 28. The osteosynthesis plate 28 does not have to be a part of the device, however. Instead, standard osteosynthesis plates can also be used with a device according to the invention having bone screws 1 and caps 5, 6, 7, 8, 9. The osteosynthesis plate 28 can have six holes 30 for screwing the osteosynthesis plate 28 to the bone screws 1. A different number of holes 30 is naturally also possible, wherein at least two holes 30, and preferably at least four holes 30, should be present for affixing a fracture. The holes 30 can have an inner diameter that is smaller than the outer diameter of the screw heads 3, but which is larger than the outer diameter of the outer thread 2, so that the bone screws 1 can be inserted up to the screw heads 3 through the holes 30 of the osteosynthesis plate 28 and the osteosynthesis plate 28 is affixable with the bone screws 1. The osteosynthesis plate 28 can have a geometry in the region of the holes 30 that is formed to fit the distal surface of the screw heads 3. The bone screws 1 can however also be easily used for connecting and affixing multiple parts of a fractured bone without an osteosynthesis plate 28. Therefore, a device according to the invention does not have to have an osteosynthesis plate 28.

The bone screws 1 can have four fluid outlet openings 32 that extend in the radial direction of the bone screw 1 in the region of the distal screw end 4. The fluid outlet openings 32 can open out into four axial grooves 34 in the outer thread 2 of the bone screws 2, which extend up to the screw head 3 and open out there in at least four radial grooves 36 on the screw head 3. The groove base of the axial grooves 34 can in this case be deeper than the thread base of the outer thread 2, so that the pharmaceutical fluid can flow along the axial grooves 34. The radial grooves 36 can extend up to the radial edge of the screw head 3. The radial grooves 36 and the osteosynthesis plate 28 thus form a conduit for discharging the pharmaceutical fluid or directing it further, when the bone screws 1 are connected to the osteosynthesis plate 28. The hose 44 for discharging fluid or the tube 16 or one of the tubes 20 can be connected to the axial grooves 34 for this purpose. In a similar way, the axial grooves 34 can together with the surrounding bone tissue form one conduit respectively for directing through the pharmaceutical fluid. Instead of four fluid outlet openings 32 and four axial grooves 34, just one fluid outlet opening and one axial groove or any number of fluid outlet openings and axial grooves can be used. Multiple fluid outlet openings 32 are preferred, however, so that the pharmaceutical fluid can exit in different radial directions in the bore hole in the bone and be available for treatment on all sides.

In the interior of the bone screws 1, a continuous conduit 38 can extend in the axial direction from the screw head 3 through to the fluid outlet openings 32. The conduit 38 in the bone screw 1 serves to direct the pharmaceutical fluid from the screw head 3 through the bone screw 1 to the fluid outlet openings 32. The axial conduit 38 can have an enlarged diameter in the screw head 3 to enable a connection to the caps 5, 6, 7, 8, 9. In the screw head 3, the axial conduit 38 can have a hex or another broken symmetry as a drive of the bone screw 1, in order to be able to operate the bone screws 1 and/or to be able to detachably affix the caps 5, 6, 7, 8, 9 and the locking caps 22, 26 to the screw head 3. For this purpose, the caps 5, 6, 7, 8, 9 and the locking caps 22, 26 can have connecting elements 39 in the form of protrusions on their proximal lower side. The connecting elements 39 can form pin-shaped protrusions. The connecting elements 39 can form a negative form of the conduit 38 in the screw head 3, such as a hex geometry. In this way, the caps 5, 6, 7, 8, 9 and the locking caps 22, 26 can be affixed on the screw heads 3 by being inserted into the screw heads 3 of the bone screws 1.

In the interior of the caps 5, 6, 7, 8, 9, conduits 40 can be disposed, which extend from the inlet openings of the caps 5, 6, 7, 8, 9 into the connecting elements 39 of the caps 5, 6, 7, 8, 9. The conduits 40 of the caps 5, 6, 7, 8, 9 are only visible in the cross-section drawings in FIGS. 2, 6 and 8, but are also disposed inside the caps 5, 6, 7, 8, 9 according to FIGS. 1 and 3 to 5 and 7, although there, they are not visible in the drawings. The conduits 40 in the caps 5, 6, 7, 8, 9 preferably open out into openings in the connecting elements 39 such that a fluid-permeable connection is present between the inlet opening of the caps 5, 6, 7, 8, 9 and the fluid outlet openings 32 of the bone screws 1, when the caps 5, 6, 7, 8, 9 with the connecting elements 39 are inserted in the wide sections of the conduits 38 of the bone screws 1 and are detachably affixed there. As a result, it is possible to introduce the pharmaceutical fluid through the caps 5, 6, 7, 8, 9 into the conduit 38 and from there, to direct it through to the fluid outlet openings 32 within the screw body or within the bone screws 1.

On the distal lower side of the caps 5, 6, 7, 8, 9, multiple radially aligned grooves 42 can be disposed. These radial grooves 42 of the caps 5, 6, 7, 8, 9 can be connected to the radial grooves 36 on the screw heads 3 in a fluid-permeable manner, when the caps 5, 6, 7, 8, 9 are connected to the screw heads 3. The grooves 42 can further be connected in a fluid-permeable manner to the hose 44 for discharging fluid or to the tube 20 or the tube 16. As a result, the pharmaceutical fluid can be removed from the radial grooves 42 and possibly directed to a further cap 5, 6, 7, 8, 9.

Pins 48 can be disposed on the distal side of the connecting elements 39 of the locking caps 22, 26. These pins 48 preferably have a negative form of the conduits 38 and thus completely fill out the conduits 38 of the bone screws 1, so that no foreign bodies can penetrate into the conduits 38 when the pins 48 fill out the conduits 38. The locking cap 22 is preferably used to lock the conduit 38 of a bone screw 1 and to screw in the bone screw 1, while the locking cap 26 is preferably used to lock the conduit 38 of a bone screw 1 that is no longer used for flushing in the screwed-in state. The locking cap 26 can thus be provided for use below the soft tissue, while the locking cap 22 can be used when screwing in a bone screw 1.

The tubes 16, 18 can form a line 50 in their interior, through which the pharmaceutical fluid can be directed from the cap 7 to the cap 8. Equally, the tubes 20 can form lines 52 in their interior, through which the pharmaceutical fluid can be introduced into the cap 9 or directed further from the cap 9.

A conveyor apparatus 56 can be disposed on or connected to a hose 54 for feeding the pharmaceutical fluid into a cap 5, 6, 7, 8, 9, as is shown schematically in FIGS. 9 to 12. A container 57 in the form of a syringe with a piston 58 for pressing out the content of the syringe can be inserted or is already inserted into the conveyor apparatus 56. The piston 58 can be movably disposed in the axial direction in the syringe and be sealed in a fluid-tight manner against the interior wall of the container 57. The conveyor apparatus 56 can have a housing 60 made of plastic, which can completely or partially close off the interior of the conveyor apparatus 56 from the outside. A securing bolt 62 can be inserted into an opening on the proximal end of the housing 60.

On the distal side of the conveyor apparatus 56, a mount 64 can be disposed for affixing the proximal end of the hose 54. For this purpose, a mounting disk 65 can be affixed on the hose 54, which can engage in the mount 64.

A conveyor plate 66 can be disposed in the conveyor apparatus 56 for pressing the piston 58 into the container 57. The conveyor plate 66 can be arrested against the housing 60 with the securing bolt 62. For this purpose, an eyelet can protrude on the proximal side of the conveyor plate 66 out of the housing 60 of the conveyor apparatus 56 and the conveyor plate 66 can be arrested against the housing 60 by inserting the securing bolt 62. The conveyor plate 66 can be driven by two tensioned springs 68. The two springs 68 are an energy storage element, in which at least the energy is stored that is required for pressing out a pharmaceutical fluid from the container 57 and through the hose 54 and through the conduits 38, 40 connected to the hose 54 (possibly also through the connected lines 50, 52), through the bone screw(s) 1 that is or are connected and screwed into the bone of a patient, out from said bone screw(s) and along the grooves 34, 36 through to the screw head 3 or past the screw head 3. Preferably, the spring force of the springs 68 can also be sufficient to remove the pharmaceutical fluid through a connected hose 44 for discharging fluid or corresponding tubes and discharge it out of the patient again.

The springs 68 can be affixed on their distal ends to the housing 60 with pins 70. On their proximal ends, the springs 68 can be affixed with pins 72 to the conveyor plate 66. The springs 68 can thus be tensioned between the pins 70 and the pins 72.

In the interior of the housing 60, a holder 74 can be formed for the container 60 and a displacement 76 can be formed for the piston 58. The container 60 can be affixed in the conveyor apparatus 56 by the form of the holder 74. The conveyor plate 66 can in this manner be pulled by the springs 68 from the proximal end through to the distal end of the displacement 76 (see FIGS. 11 and 12). The piston 58 in the conveyor apparatus 56 with the conveyor plate 66 can be pressed into the container 60 driven by the springs 68 when the securing bolt 62 has been removed and the valve element 59 is open. As a result, pharmaceutical fluid contained in the container 57 can be pressed out of the container 57 and through the hose 54 and through connected caps 5, 6, 7, 8, 9, 22, 26 and bone screws 1. The pressure acting on the pharmaceutical fluid can possibly also be used to drive a flushing circuit of the pharmaceutical fluid, which leads out of the bone of the patient or out of the body of the patient.

Depending on the application, an aqueous solution comprising at least one antibiotic and/or at least one antimycotic ingredient can be used as the pharmaceutical fluid to be applied. Further, the medical fluid can also contain at least one cytostatic and/or at least one chemotherapeutic ingredient.

For a medical application of the devices according to the invention, the bone screws and preferably also the caps 5, 6, 7, 8, 9, and osteosynthesis plates 28 possibly present, can be constructed of biocompatible materials, in which radiopaque materials are contained, so that their position is determinable using X-ray imaging procedures.

An exemplary application of the devices according to the invention is described below. The bone screws 1 are screwed into a bone (not shown) and here, the position of the bone screws 1 relative to each other is secured using an osteosynthesis plate 28. Here, two or more parts of a fractured bone can be affixed to each other. The bone screws 1 can here be locked with locking caps 22, 26. The bone screws 1 can here be directed through the holes 30 of the osteosynthesis plate 28 and screwed into the osteosynthesis plate 28 through to the stop of the screw heads 3.

Then, the locking caps 22, 26 are removed and instead, caps 5, 6, 7, 8, 9 are inserted into the free conduits 38 of the bone screws 1 and connected there. The caps 5, 6, 7, 8, 9 create a fluid-permeable connection between the inlet openings of the caps 5, 6, 7, 8, 9 and the conduits 38 of the bone screws 1. Via the lines 50, 52 of the tubes 16, 18, 20 or via the hoses 10, 12, 14, 44, 46, 54, the inlet openings of the caps 5, 6, 7, 8, 9 can be interconnected and connected to the container 57. The conveyor apparatus 56 is here disposed outside the body of the patient and the hose 54 is directed inside for feeding fluid into the patient. The pharmaceutical fluid can be pressed in with the conveyor apparatus 56 via the hose 54 and at least one of the hoses 10, 14, 46 for feeding fluid into at least one of the caps 5, 6, 7, 8, 9. From there, the pharmaceutical fluid can be pressed out through the conduit 40 or the conduits 40 of at least one of the caps 5, 6, 7, 8, 9 into the conduit 38 of at least one bone screw 1, and there out of the fluid outlet openings 32 of the at least one bone screw 1. There, the pharmaceutical fluid flows along the axial grooves 34 on the bone to the radial grooves 36, and there through the radial grooves 36 into the radial grooves 42 of the caps 5, 6, 7, 8, 9. From there, the pharmaceutical fluid can be discharged through the hose 44 for discharging fluid or through the tube 16, 20. The pharmaceutical fluid can here be directed out of the body or through a further cap 5, 6, 7, 8, 9 and a further bone screw 1. The discharged pharmaceutical fluid can be examined in order to check on the success of the treatment, and depending on the result, the treatment can be adjusted by modifying the composition and/or through-flow quantity of the pharmaceutical fluid. Alternatively, the pharmaceutical fluid exits from the radial grooves 42 of the caps 5, 6, 7, 8, 9 and is reabsorbed in the body away from the bones to be treated.

With the device according to the invention, therefore, flushing with a pharmaceutical fluid can be produced, wherein the pharmaceutical fluid can be adjusted to the treatment situation at any time. Due to the grooves 34, 36, 42, no pressure of the pharmaceutical fluid can build up inside the bone. As a result, irritation of the tissue to be treated and embolisms can be prevented.

The features of the invention disclosed in the preceding description, as well as in the claims, figures and exemplary embodiments, can be essential both individually and in any combination for realizing the invention in its various embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

What is claimed:

1. A device for the local application of and/or for flushing with pharmaceutical fluids, the device comprising:
    at least one bone screw having a screw body in which is disposed at least one conduit, an outer thread with a base, and a proximal screw head, wherein the at least one conduit is fluid-permeable, begins at the screw head and opens out into at least one fluid outlet opening in the screw body, wherein the at least one fluid outlet opening is spaced apart from the screw head in a distal direction;
    at least one axial groove in the screw body having a base and penetrating the outer thread of the bone screw, which at least one axial groove extends from the at least one fluid outlet opening in the screw body through to at least a lower side of the screw head, wherein the base of the at least one axial groove is deeper in the screw body than the base of the outer thread;
    at least one cap with an inlet opening and with a connecting element for the detachable connection of the at least one cap with the screw head of the at least one bone screw, wherein a fluid-permeable conduit is arranged in the at least one cap and opens out into the at least one conduit of the at least one bone screw when the at least one cap is detachably connected via the connecting element to the at least one bone screw, and wherein the fluid-permeable conduit begins at, and is open to, the inlet opening in the at least one cap; and
    at least one hose for feeding fluid, which is connected or connectable in a fluid-permeable manner with the inlet opening on one of the at least one cap so that the pharmaceutical fluid is pressable from the at least one fluid outlet opening with a pressure through the at least one feeding hose, through the fluid-permeable conduit of the at least one cap, and through the at least one conduit of the at least one bone screw when the at least one feeding hose is connected to the at least one cap and the at least one cap is connected via the connecting element with the at least one bone screw.

2. The device according to claim 1, wherein the screw head has a surface and the at least one bone screw has at least one radial groove which is disposed in the surface of the screw head of the at least one bone screw and which is connected to the at least one axial groove in the screw body.

3. The device according to claim 1, wherein the screw head has a distal side and the at least one axial groove penetrating the outer thread of the bone screw extends from the at least one fluid outlet opening in the screw body through to the distal side of the screw head.

4. The device according to claim 1, wherein the cap has a lower side and the connecting element is a protrusion on the lower side of the cap pointing to the screw head, wherein the protrusion comprises the fluid-permeable conduit in the at least one cap, wherein the at least one cap is reversibly inserted or insertable into the at least one conduit of the at least one bone screw with the protrusion.

5. The device according to claim 4, further comprising a discharge hose and wherein the at least one cap has a radial edge and a lower side pointing to the screw head with a groove that extends radially outward from the protrusion, wherein the groove of the at least one cap extends up to the radial edge of the at least one cap and/or the discharge hose is connected in a fluid-permeable manner to the groove of the at least one cap for discharging fluid.

6. The device according to claim 1, further comprising a fluid reservoir containing the pharmaceutical fluid wherein the at least one feeding hose is connected or connectable to the fluid reservoir in a fluid-permeable manner, wherein the pharmaceutical fluid from the fluid reservoir is pressable under pressure into the at least one feeding hose for feeding fluid through the fluid-permeable conduit of the at least one cap and into the at least one conduit of the at least one bone screw.

7. The device according to claim 1, wherein, although connected to the at least one fluid outlet opening, the at least one conduit in the screw body is not connected to the at least one axial groove in the screw body.

8. The device according to claim 1, wherein the at least one cap is formed as a cupola with an underside that is planar with the exception of the connecting element and/or the at least one cap fully covers the screw head.

9. The device according to claim 1, further comprising a discharge hose, wherein the at least one cap has a lower side pointing toward the screw head and at least one discharge opening disposed on the lower side of the cap for discharging fluids, the at least one discharge opening connectable or connected to the discharge hose.

10. The device according to claim 1, further comprising a discharge hose for discharging fluid and wherein the at least one feeding hose and the discharge hose are interconnected in a longitudinal direction or are interconnected parallel adjacent to each other or are disposed coaxially in relation to each other.

11. The device according to claim 1, further comprising at least one osteosynthesis plate.

12. The device according to claim 11, wherein the at least one cap has a lower side pointing towards the screw head and at least one latching element engaging the at least one osteosynthesis plate.

13. The device according to claim 1, further comprising a discharge hose for discharging fluid and wherein the at least one feeding hose and the discharge hose each have a maximum radial expansion of 5 percent with an inner pressure of 5 bar.

14. The device according to claim 1, further comprising one tube or two tubes wherein the at least one cap is at least two caps and the at least one bone screw is at least two bone screws, wherein the at least two caps are affixed with their connecting elements in two different of the at least two bone screws, and wherein the at least two caps are interconnected via the one tube or the two tubes in a fluid-permeable manner.

15. The device according to claim 14, further comprising a discharge hose for discharging fluid and wherein the at least one feeding hose for feeding fluid is only connected to one of the at least two caps and wherein the pharmaceutical fluid is distributable over the at least two bone screws via the at least two caps that are interconnected via the one tube or the two tube, or
the at least one feeding hose and the discharge hose are only connected to one of the at least two caps in a fluid-permeable manner and wherein the pharmaceutical fluid is serially directable through the at least two bone screws via the at least two caps that are interconnected via the one tube or the two tubes.

16. The device according to claim 1, further comprising a container for the pharmaceutical fluid and wherein the pharmaceutical fluid includes at least one antibiotic active ingredient, at least one antimycotic active ingredient, at least one chemotherapeutic ingredient, or a combination of two or all three of those ingredients.

17. The device according to claim 16, further comprising a manually operable valve element for regulating the flow speed of the pharmaceutical fluid and wherein the container is a hollow cylinder having a first end and a delivery opening on an end positioned opposite the first end with a piston that is axially movable in the hollow cylinder, the piston closing the first end of the hollow cylinder and the delivery opening being connected or connectable to the at least one feeding hose via the manually operable valve element.

18. The device according to claim 1, further comprising an area surrounding the at least one bone screw, a container for the pharmaceutical fluid, and a conveyor connected or connectable to the container for pressing the pharmaceutical fluid out of the container and into the at least one feeding hose through the fluid-permeable conduit in the at least one cap, through the at least one conduit in the screw body of the at least one bone screw, and through the at least one fluid outlet opening into the area surrounding the at least one bone screw.

19. The device according to claim 18, further comprising an energy storage element providing energy to drive the conveyor.

20. The device according to claim 1, further comprising at least one locking cap with a proximal pin, the at least one locking cap reversibly locking the at least one conduit in the screw body of the bone screw to the at least one fluid outlet opening via the proximal pin.

* * * * *